(12) United States Patent
Shah et al.

(10) Patent No.: US 9,788,955 B2
(45) Date of Patent: Oct. 17, 2017

(54) TOTAL KNEE REPLACEMENT PROSTHESIS WITH HIGH ORDER NURBS SURFACES

(75) Inventors: Asit Shah, Ridgewood, NJ (US); Murali Jasti, Weston, MA (US)

(73) Assignee: Maxx Orthopedics, Inc., Plymouth Meeting, PA (US)

( * ) Notice: Subject to any disclaimer, the term of this patent is extended or adjusted under 35 U.S.C. 154(b) by 324 days.

(21) Appl. No.: 12/388,125

(22) Filed: Feb. 18, 2009

(65) Prior Publication Data

US 2009/0319049 A1  Dec. 24, 2009

Related U.S. Application Data

(60) Provisional application No. 61/029,457, filed on Feb. 18, 2008, provisional application No. 61/029,438, filed on Feb. 18, 2008.

(51) Int. Cl.
*A61F 2/38* (2006.01)
*A61F 2/30* (2006.01)

(52) U.S. Cl.
CPC .............. *A61F 2/3886* (2013.01); *A61F 2/38* (2013.01); *A61F 2/3094* (2013.01); *A61F 2002/302* (2013.01); *A61F 2002/30518* (2013.01); *A61F 2002/30878* (2013.01); *A61F 2220/0025* (2013.01); *A61F 2230/0065* (2013.01); *A61F 2310/00023* (2013.01); *A61F 2310/00029* (2013.01)

(58) Field of Classification Search
CPC ........ A61F 2/3886; A61F 2/38; A61F 2/3094; A61F 2002/302; A61F 2002/30518

USPC ............................................. 623/20.14–20.36
See application file for complete search history.

(56) References Cited

U.S. PATENT DOCUMENTS

| | | | | |
|---|---|---|---|---|
| 4,309,778 A * | 1/1982 | Buechel et al. | ........... | 623/20.29 |
| 5,011,496 A * | 4/1991 | Forte et al. | ................ | 623/20.27 |
| 5,116,375 A * | 5/1992 | Hofmann | .................... | 623/20.27 |
| 5,147,405 A * | 9/1992 | Van Zile et al. | ........... | 623/20.27 |
| 5,370,699 A * | 12/1994 | Hood et al. | ................ | 623/20.28 |
| 5,549,686 A * | 8/1996 | Johnson et al. | ........... | 623/20.27 |
| 5,549,688 A * | 8/1996 | Ries | ...................... | A61F 2/3859 623/20.35 |
| 5,964,808 A * | 10/1999 | Blaha | ........................ | A61F 2/38 623/20.28 |
| 6,123,729 A * | 9/2000 | Insall et al. | ................ | 623/20.31 |
| 6,325,828 B1 * | 12/2001 | Dennis | .................. | A61F 2/3868 623/20.14 |

(Continued)

*Primary Examiner* — Alvin Stewart
(74) *Attorney, Agent, or Firm* — Ryder, Lu, Mazzeo & Konieczny LLC; Joseph M. Konieczny Sr.; Gregory J. Gore

(57) ABSTRACT

A knee replacement prosthesis comprising a femoral component and a tibial component that enable anterior-posterior translation of the femur relative to the tibia and enable the tibia to rotate about its longitudinal axis during flexion of the knee. The femoral component connects to the distal end of a resected femur and includes medial and lateral condyles having distal, articulating surfaces, and a patellar flange having a patellar articulating surface. The tibial component connects to the proximal end of a resected tibia and includes a proximal bearing surface with medial and lateral concavities that articulate with the medial and lateral condyles. The condylar articulating surfaces and the said concavities are substantially defined by non-uniform, rational B-spline surfaces (NURBS).

29 Claims, 20 Drawing Sheets

(56) References Cited

U.S. PATENT DOCUMENTS

| | | | | |
|---|---|---|---|---|
| 6,660,039 B1* | 12/2003 | Evans | | A61F 2/3886 623/20.29 |
| 6,701,174 B1* | 3/2004 | Krause et al. | | 600/407 |
| 6,730,128 B2* | 5/2004 | Burstein | | 623/20.27 |
| 7,326,252 B2* | 2/2008 | Otto et al. | | 623/20.15 |
| 7,678,152 B2* | 3/2010 | Suguro et al. | | 623/20.27 |
| 7,731,755 B2* | 6/2010 | Wyss et al. | | 623/20.27 |
| 7,881,768 B2* | 2/2011 | Lang | | A61B 5/055 600/407 |
| 7,922,771 B2* | 4/2011 | Otto et al. | | 623/20.31 |
| 8,337,564 B2* | 12/2012 | Shah | | A61F 2/38 623/20.15 |
| 8,480,752 B2* | 7/2013 | Dun | | A61F 2/3886 623/20.15 |
| 8,636,807 B2* | 1/2014 | Komistek | | A61F 2/3886 623/20.27 |
| 8,911,502 B2* | 12/2014 | Li | | A61F 2/38 623/20.14 |
| 2002/0010512 A1* | 1/2002 | Takei | | A61F 2/3886 623/20.31 |
| 2003/0009228 A1* | 1/2003 | Meyers et al. | | 623/20.24 |
| 2003/0023314 A1* | 1/2003 | Burstein | | 623/20.27 |
| 2003/0055500 A1* | 3/2003 | Fell et al. | | 623/14.12 |
| 2003/0216669 A1* | 11/2003 | Lang et al. | | 600/587 |
| 2004/0054416 A1* | 3/2004 | Wyss et al. | | 623/20.27 |
| 2004/0102866 A1* | 5/2004 | Harris et al. | | 700/117 |
| 2004/0162620 A1* | 8/2004 | Wyss | | 623/20.27 |
| 2004/0204760 A1* | 10/2004 | Fitz | | A61F 2/30756 623/14.12 |
| 2004/0227761 A1* | 11/2004 | Anderson et al. | | 345/473 |
| 2004/0236424 A1* | 11/2004 | Berez et al. | | 623/14.12 |
| 2005/0168460 A1* | 8/2005 | Razdan et al. | | 345/419 |
| 2005/0209701 A1* | 9/2005 | Suguro | | A61F 2/3886 623/20.27 |
| 2005/0267584 A1* | 12/2005 | Burdulis et al. | | 623/20.19 |
| 2006/0265080 A1* | 11/2006 | McMinn | | 623/20.27 |
| 2007/0100462 A1* | 5/2007 | Lang et al. | | 623/20.29 |
| 2007/0135926 A1* | 6/2007 | Walker | | A61F 2/3859 623/20.31 |
| 2007/0198022 A1* | 8/2007 | Lang et al. | | 606/88 |
| 2008/0009950 A1* | 1/2008 | Richardson | | A61F 2/3868 623/20.29 |
| 2008/0030497 A1* | 2/2008 | Hu et al. | | 345/419 |
| 2008/0119940 A1* | 5/2008 | Otto et al. | | 623/20.31 |
| 2008/0140212 A1* | 6/2008 | Metzger | | A61F 2/3886 623/20.31 |
| 2008/0243258 A1* | 10/2008 | Sancheti | | 623/20.21 |
| 2008/0243259 A1* | 10/2008 | Lee et al. | | 623/20.32 |
| 2009/0036992 A1* | 2/2009 | Tsakonas | | 623/20.14 |
| 2009/0043396 A1* | 2/2009 | Komistek | | A61F 2/3886 623/20.32 |
| 2009/0210066 A1* | 8/2009 | Jasty | | A61F 2/3886 623/20.31 |
| 2009/0306785 A1* | 12/2009 | Farrar | | A61F 2/3859 623/20.27 |
| 2009/0319049 A1* | 12/2009 | Shah | | A61F 2/38 623/20.31 |
| 2010/0016978 A1* | 1/2010 | Williams | | A61F 2/3868 623/20.27 |
| 2010/0016979 A1* | 1/2010 | Wyss | | A61F 2/3886 623/20.27 |
| 2010/0036499 A1* | 2/2010 | Pinskerova | | 623/20.31 |
| 2012/0197409 A1* | 8/2012 | McKinnon | | A61F 2/3886 623/20.27 |
| 2012/0245699 A1* | 9/2012 | Lang et al. | | 623/20.3 |
| 2012/0310362 A1* | 12/2012 | Li | | A61F 2/38 623/20.32 |
| 2014/0257508 A1* | 9/2014 | Bojarski | | A61F 2/3859 623/20.35 |
| 2015/0230874 A1* | 8/2015 | Musuvathy | | A61B 19/50 703/1 |

* cited by examiner

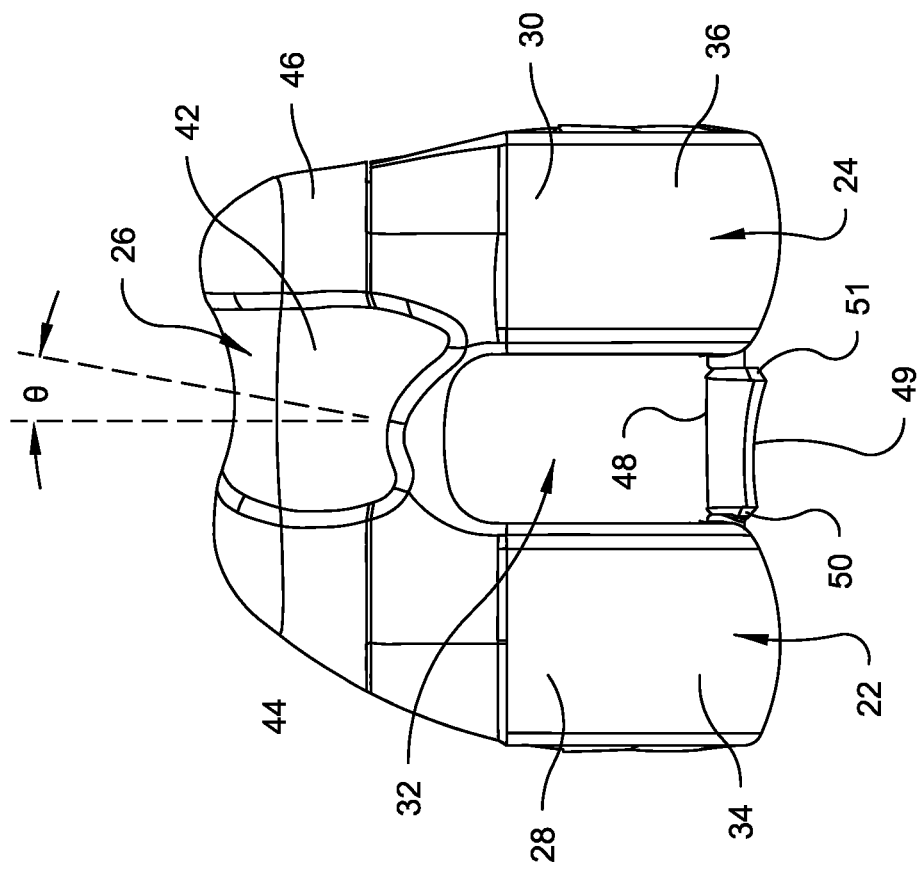
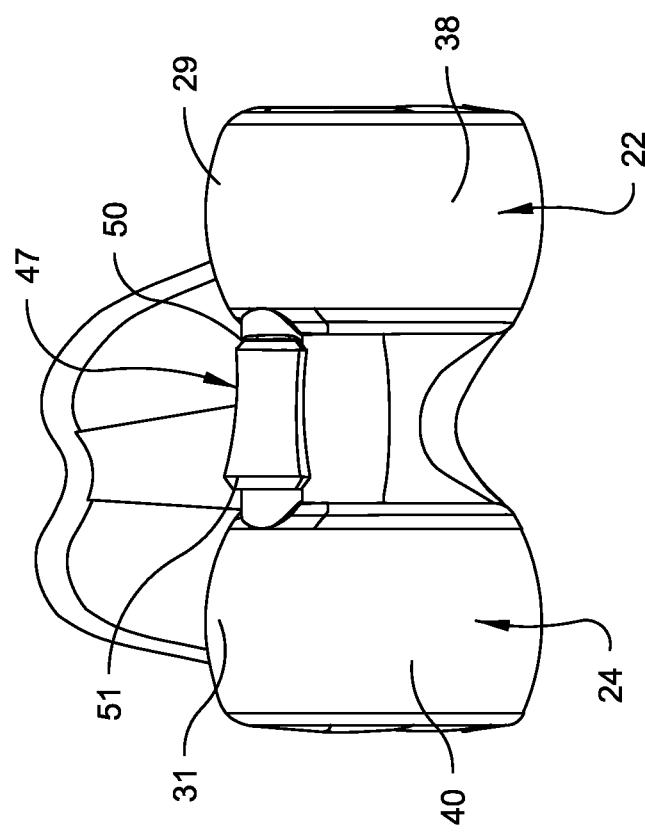

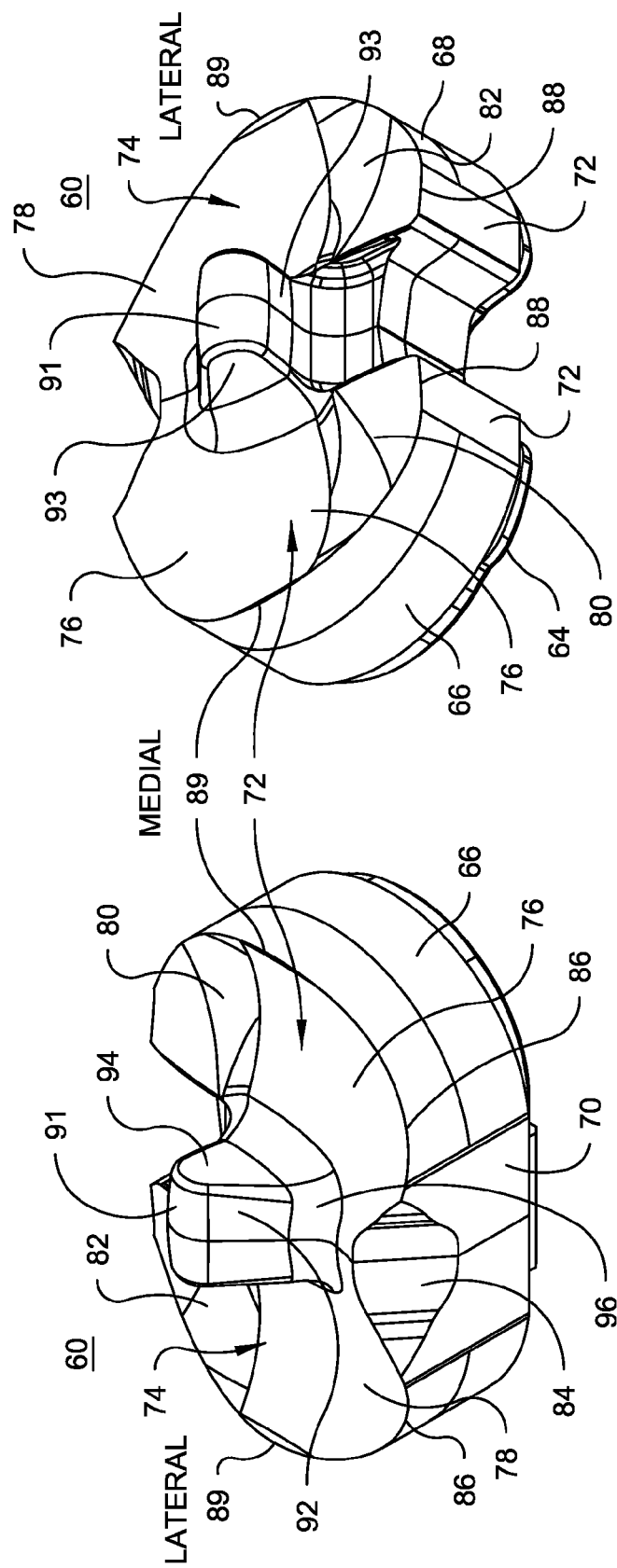

TOTAL KNEE REPLACEMENT PROSTHESIS WITH HIGH ORDER NURBS SURFACES

RELATED APPLICATIONS

This is a nonprovisional application claiming priority to U.S. provisional application No. 61/029,438 filed Feb. 18, 2008 entitled Total Knee Replacement Prosthesis with High Order NURBS Surfaces, incorporated herein by reference, and U.S. provisional application No. 61/029,457 filed Feb. 18, 2008 entitled Total Knee Replacement Prosthesis, incorporated herein by reference.

FIELD OF THE INVENTION

The present invention relates to a knee replacement prosthesis, in particular, a prosthetic knee implant having articulating surfaces defined by non-rational, uniform, B-spline surfaces (NURBS) that more accurately mimic the function and movement of the natural knee.

BACKGROUND OF THE INVENTION

While seemingly simple to the casual observer, the human knee articulates along a complex path. As the knee is flexed, the tibia obviously rotates (flexes) about a coronal axis relative to the femur. However, the femur also translates posteriorly on the tibia and the tibia also rotates about its longitudinal axis. Further, as the knee is flexed, the patella is drawn medially. The complex articulation path of the human knee is dictated primarily by the geometry of the distal femur and proximal tibia. For example, the medial femoral condyle is shorter and spherical in shape, while the lateral femoral condyle is longer and ellipsoidal in shape. The medial tibial condyle is concave whereas the lateral condyle is convex.

The complex path of articulation of the human knee is also dictated by the arrangements of ligaments surrounding and connecting the distal femur and proximal tibia. The human knee is complemented by two collateral ligaments, one on the lateral side of the joint and the other on the medial side thereof. Each ligament is attached to the tibia and the femur. The attachment points to the femur are approximately on the axis of the arc along which the other end of the tibia moves and the knee flexes. The collateral ligaments provide stability to the knee in varus and valgus stresses.

The human knee further includes two cruciate ligaments in the middle of the knee joint. One cruciate ligament is attached to the posterior margin of the tibia, while the other is attached towards the anterior margin of the tibia. Both ligaments are attached to the femur in the notch between the condyles approximately on the axis of the collateral ligaments. The cruciate ligaments provide stability in the anterior and posterior direction, and also allow the knee to rotate axially, i.e., about its longitudinal axis. Thus, as the knee is flexed, the tibia undergoes internal rotation about its longitudinal axis.

Known total knee replacement prostheses generally consist of a femoral component and a tibial component, which are attached to the resected surfaces of the distal femur and the proximal tibia, respectively, either by pressure fitting or by adhering with polymethyl methacrylate bone cement. Each component includes a pair of condylar surfaces that compliment one another and allow the components to articulate relative to one another. The geometry of the complimenting condylar surfaces determines the complexity of movement and degrees of freedom, namely, whether the components can flex, translates and/or rotate relative to one another. The femoral component also includes a patellar flange, which articulates either with the natural patella or an artificial patellar component. The patellar flange provides the lever arm for the quadriceps muscle.

Known total knee prostheses do not accurately replicate the condylar surfaces of the human knee. For example, the femoral condylar surfaces of known prostheses are generally convex and rounded in the medial-lateral direction and anterior-posterior direction. The radius of curvature in the anterior-posterior direction is larger than the radius of curvature in the medial-lateral direction. Generally, the arc center of the sagittal curvature of the distal and posterior aspects of condyles are centered on the axis joining the medial and lateral epicondyles, so that the tension in the collateral ligaments, which attach to the epicondyles, remains nearly constant in flexion and extension. The tibial surfaces are generally concave and dish-shaped with their major axis aligned in the sagittal plane. The sagittal and coronal radii of the tibial condyles are greater than the sagittal and coronal radii of the femoral condyles, which provides some degree of rotational laxity. Likewise, the patellar flange on the femur is concave and oriented from superior to inferior direction with a radius of coronal curvature greater than that of the dome shaped patella.

The design of many prior art total knee replacement components ignore the complex rotational movements of the natural knee in favor of a simple hinge design, which allows only pivotal rotation about a single horizontal axis. Such simple designs have largely been abandoned because of high loosening rates associated with the high rotational stresses placed on the prosthetic components. Other prior art knee prostheses attempt to more closely mimic the motion path of the natural knee. However, these prostheses do not accurately replicate the natural motion path of the human knee and have other manufacturing and durability limitations.

Therefore, it would be desirable to provide a knee replacement prosthesis, which replicates the motion of the natural knee by allowing femoral translation and tibial rotation as the knee is flexed, and which is easy and inexpensive to manufacture.

Many of the prior art knee replacement prostheses are modeled using simple geometries such as circles, arcs, lines, planes, spheres, and cylinders, which have well defined lengths and radii of curvature. However, the complex motion path of the human knee can not be replicated using simple geometries. Prostheses modeled using simple geometries produce unnatural motion, undue tension and pain in the ligaments, and increased wear and loosening of the prosthetic components. Therefore, higher order geometries are needed to generate the complex motion path of the human knee.

Higher order surfaces such as B-spline or Bezier surfaces are much more versatile in describing three dimensional shapes of complex surfaces. A non-uniform rational B-spline surface, or NURBS, is a biparameter surface defined with spline transformations between parameter space and 3D space. NURBS modeling is used in computer graphics for generating and representing curves and surfaces. For example, NURBS is used in CAD modeling software such as those developed by McNeil and associates (Rhinoceros 3D), and Unigraphics (IDEAS). A diagrammatic representation of a NURBS surface is shown in FIG. 25 labeled prior art.

NURBS surface has two independent variables, u and v, and four dependent variables, $x(s,t)$, $y(s,t)$, $z(s,t)$, and $d(s,t)$, such that $$\vec{S}(u, v) = (x(u, v)/d(u, v), y(u, v)/2(u, v), z(u, v)/d(u, v))$$

$$\vec{S}(u, v) = \frac{\sum_{i=0}^{n}\sum_{j=0}^{m} w_{ij}\vec{P}_{ij}N_{i,p}(u)N_{j,q}(v)}{\sum_{i=0}^{n}\sum_{j=0}^{m} w_{ij}\vec{N}_{i,p}(u)N_{j,q}(v)}$$

where the B-spline shape functions N(u) are defined to be:

$$N_{i,0}(u) = \begin{Bmatrix} 1 & u_i \le u < u_{i+1} \\ 0 & \end{Bmatrix};$$

$$N_{i,p}(u) = \frac{u - u_i}{u_{i+p} - u_i}N_{i,p-1}(u) + \frac{u_{i+p+1} - u}{u_{i+p+1} - u_{i+1}}N_{i+1,p-1}(u);$$

given the knot vector $u_i = u_0; u_1; \ldots ; u_m$

NURBS modeling is very useful in manufacturing. The three dimensional shape of NURBS surfaces can be readily altered simply by changing the location of the control points. Furthermore, boundary representation solids can be generated with these surfaces, which are easily manufactured. Additionally, the NURBS data can be input into many computer-controlled manufacturing and production machines to program tool paths. Therefore, it would be desirable to provide a knee replacement prosthesis having high order surface geometries generated using NURBS modeling, which replicate the motion of the natural knee and which can be easily manufactured using programmable manufacturing equipment.

SUMMARY OF THE INVENTION

The invention provides a total knee replacement prosthesis that mimics the motion of the natural knee by allowing femoral translation and tibial rotation as the knee is flexed. The novel prosthesis comprises a femoral component that articulates with a tibial component and the natural or prosthetic patella. The components are modeled using higher order topography to create complimenting, articulating surfaces that allow flexion, translation and rotation under physiologic load to replicate the motion path of the natural knee.

In a first embodiment, the knee replacement prosthesis comprises a femoral component that connects to the distal end of a resected femur and a tibial component that connects to the proximal end of a resected tibia. The femoral component includes medial and lateral condyles having distal, articulating condylar surfaces, and a patellar flange having an articulating patellar surface. The tibial component includes a proximal bearing surface with medial and lateral concavities that articulate with the medial and lateral condyles. The condylar surfaces and concavities are substantially defined by high order nonrational B-spline surfaces (NURBS), which enable anterior-posterior translation of the femur relative to the tibia, and which enable the tibia to rotate about its longitudinal axis during flexion of the knee. The NURBS surfaces of the prosthesis are designed such that under weight bearing and muscular loads, the movement of the natural knee is mimicked.

In a preferred embodiment, the tibia does not rotate axially, i.e., about its longitudinal axis, as the knee is initially flexed from full extension to an intermediate position at about 30 degrees. After continued flexion past the intermediate position, the tibia then rotates axially to full flexion. When the prosthesis is fully flexed, the tibia also rotates axially about 10 degrees or more.

The condyles translate posteriorly in the concavities during flexion and translate anteriorly during extension. In a preferred embodiment, the posterior/anterior translation is about 1-2 millimeters during full flexion.

The articulating condylar surfaces and the tibial concavities have multiple radii of curvature. The tibial concavities have at least a first radius of curvature in the sagittal plane and at least a first radius of curvature in the coronal plane that is larger than said first radius of curvature. The concavities also have multiple radii of curvature in the sagittal plane. The condylar surfaces have a first radius of curvature in the anterior portion of the sagittal plane and a second radius of curvature in the posterior portion of the sagittal plane that is smaller than the first radius of curvature. Each of the anterior portion and the posterior portion of the condylar articulating surfaces may also have multiple radii of curvature in the sagittal plane. The posterior portion of each condyle is shaped to allow flexion greater than 100 degrees and more preferably more than 130 degrees.

The tibial component includes a base having distal and proximal surfaces, and a liner having a distal surface that engages the proximal surface of the base and a proximal surface forming the bearing surface that engages and articulates with the femoral component. The base comprises a base plate that rests on the tibial plateau, and a keel fixed to the distal surface of the plate that can be inserted into the proximal tibial medullary canal. Preferably, the distal surface of the base plate has a textured, roughened surface.

In the first embodiment of the invention, the prosthesis is designed for use when the posterior cruciate ligament is surgically removed. In this embodiment, the femoral component includes an asymmetric cam connecting the posterior ends of the condyles, and the tibial component includes a central, symmetric post intermediate the concavities. Anterior and posterior translation of the femoral component relative to the tibial component, as well as tibial axial rotation, is controlled by the cam and the central post. The articular NURBS surfaces enable posterior femoral rotation and internal tibial rotation as the knee is flexed.

Another embodiment of the prosthesis is designed for use when the posterior cruciate ligament is retained. In this embodiment, the femoral component does not include the cam and the tibial component does not include the central post. Anterior and posterior translation of the femoral component relative to the tibial component, as well as tibial axial rotation, is controlled by the posterior cruciate ligament. The articular NURBS surfaces enable posterior femoral rotation and internal tibial rotation as the knee is flexed.

In a further embodiment of the invention, the patellar surface is also substantially defined by NURBS surfaces and guides articulating motion of the femur on the patella. In this embodiment, the patellar flange includes an upwardly and laterally-angled patellar groove and raised trochlear surfaces on each side of the groove. The topography of the patellar flange, in particular the depth of the patellar groove, can be varied to track with either the natural patella or an artificial patellar component.

BRIEF DESCRIPTION OF THE DRAWINGS

FIG. 5 is a posterior elevation showing the posterior section of the condylar portion of the femoral component shown in FIG. 1;

FIG. 6 is an anterior elevation showing the patellar flange and the anterior section of the condylar portion of the femoral component shown in FIG. 1;

FIG. 9 is a perspective showing the anterior proximal surface of the tibial component liner of FIG. 1;

FIG. 10 is an enlarged perspective showing the posterior proximal surface of the tibial component of FIG. 1;

DETAILED DESCRIPTION OF PREFERRED EMBODIMENTS

Figure 2:
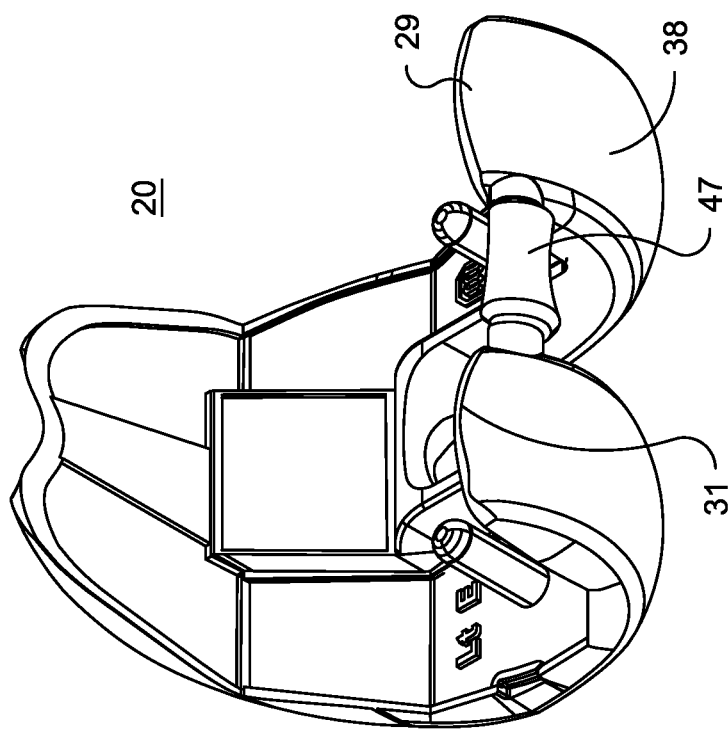
FIG. 2 is a perspective showing the proximal surface of the femoral component shown in FIG. 1.

For the purpose of illustrating the invention, several embodiments of the invention are shown in the accompanying drawings. However, it should be understood by those of ordinary skill in the art that the invention is not limited to the precise arrangements and instrumentalities shown therein and described below. Throughout the specification, like reference numerals are used to designate like elements. Numerous changes and modifications within the spirit and scope of the invention will become apparent to those skilled in the art from this detailed description.

Unless otherwise defined, all technical and scientific terms used herein in their various grammatical forms have the same meaning as commonly understood by one of ordinary skill in the art to which this invention belongs. The terms anterior, posterior, proximal, distal, medial, lateral, sagittal, coronal, and transverse are used herein with their conventional medical/anatomical meaning as defined, for example, in Dorland's Illustrated Medical Dictionary.

A knee replacement prosthesis in accordance with an embodiment of the invention is illustrated in FIGS. 1-19 and is designated generally by reference numeral 10. The prosthesis 10 includes a femoral component 20, constructed and designed to be fixed to the distal end of a resected femur, and a tibial component 52, constructed and designed to be fixed to the proximal end of a resected tibia. The components 20, 52 can be fixed to the femur and tibia, respectively, using conventional methods after conventional femoral and tibial resection. The tibial component 52 has a symmetrical design that can be used on either the left or right knee; however, the femoral component is asymmetrical and is illustrated in FIGS. 1-19 for installation on the left knee. A mirror image of the femoral component 20 will be used for installation on the right knee.

The femoral component 20 has a medial condylar portion or condyle 22, a lateral condylar portion or condyle 24, and a patellar flange portion or flange 26, which bridges the anterior ends 28, 30 of the medial 22 and lateral 24 condyles, respectively. The medial 22 and lateral 24 condyles are arranged in substantially parallel relationship to each other and define an intercondylar notch 32 there between. As the prosthesis flexes, different sections of the curved condylar portions engage and articulate with the tibial component 52.

Figure 11:
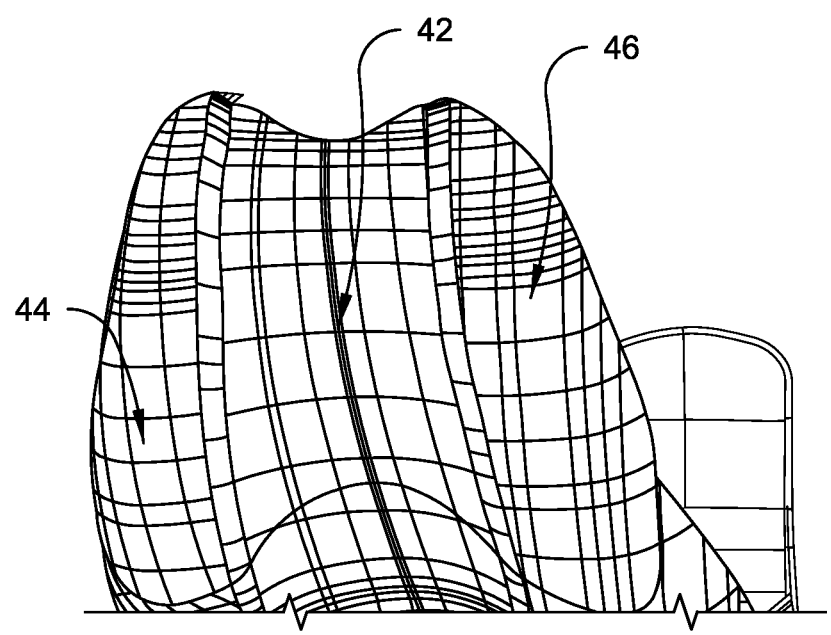
FIG. 11 is an enlarged perspective of the patellar flange portion of the femoral component illustrating with u and v isocurves the NURBS surfaces of the patellar groove, and medial and lateral trochlear portions of the patellar groove.
Figure 20:
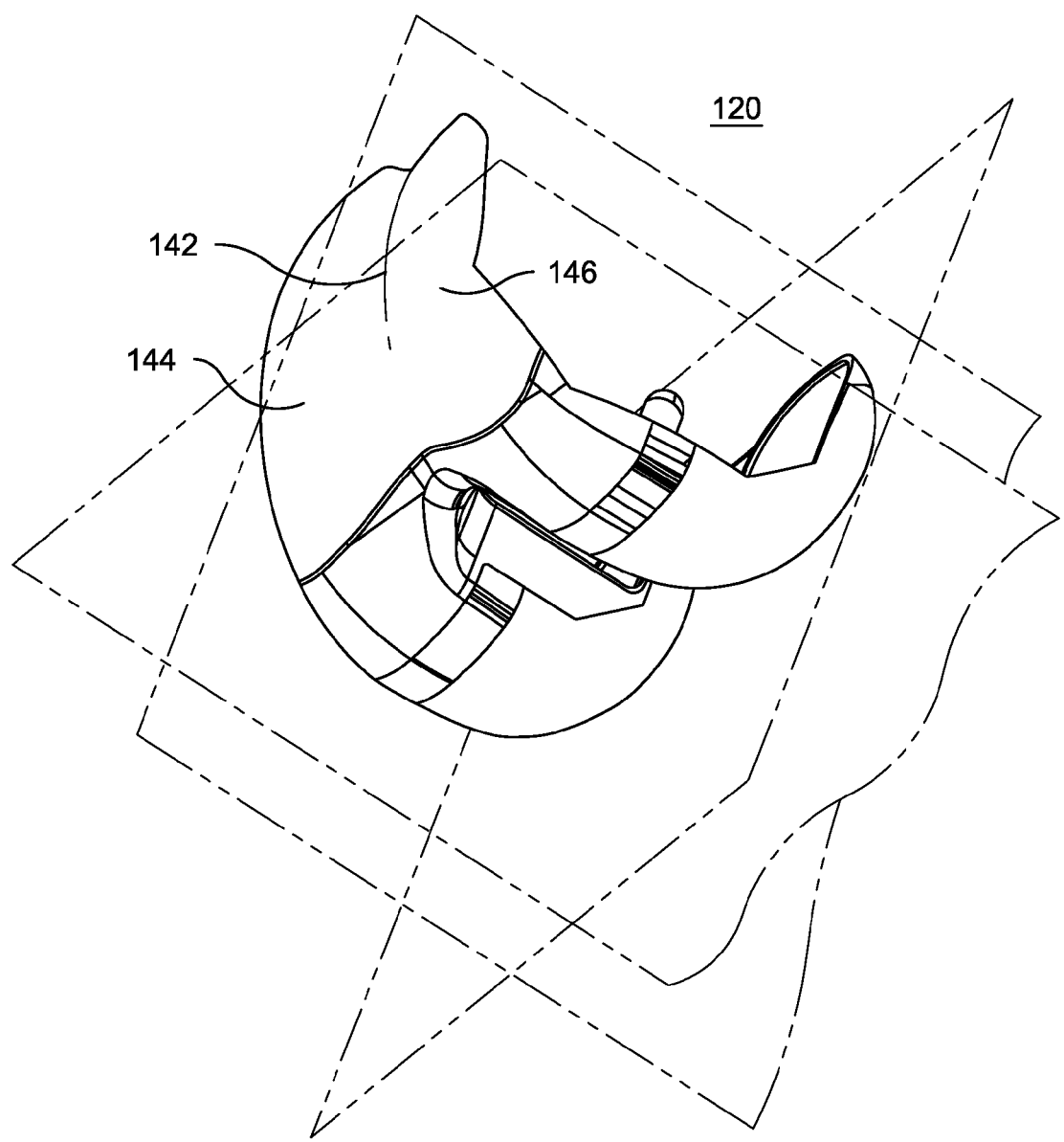
FIG. 20 is a perspective of another embodiment of a femoral component having a patellar flange formed from a single NURBS surface.

The patellar flange 26 includes a patellar groove 42, which is flanked by a medial trochlear surface 44 and a lateral 46 trochlear surface. The patellar flange is designed to articulate with either the natural patella or a patellar component. As best seen in FIG. 6, the patellar flange widens inferiorly to accommodate the patella. The trochlear surfaces 56, 58 are elevated and transition smoothly into to the patellar groove 54 to provide stability to the patella. Referring to FIG. 6, the patellar groove 42 extends upwardly and laterally at an angle theta (θ) in the coronal plane in a curvilinear fashion along with the trochlear surfaces 44, 46 to provide optimal tracking and stability. In a preferred embodiment, the angle theta (θ) is about 6 degrees. The patellar flange also transitions smoothly with the condyles 22, 24. The patellar flange is constructed by approximating the geometry of the distal anterior surface of a natural femur. As a result, the patellar flange has natural tracking of the prosthetic or natural patella. The patellar flange can be constructed from multiple NURBS surfaces, such as shown in FIG. 11, or a single NURBS surface, such as shown in FIG. 20.

Each condyle 22, 24 generally comprises an anterior 34, 36 and posterior 38, 40 surface, which blend smoothly with each other without any abrupt transition. In the embodiment shown in FIGS. 1-19, the anterior and posterior surfaces resemble toroidal sections, with each surface having its radius about the major axis (major radius) substantially in the sagittal plane. In general, the major radius of curvature of the condyles 22, 24 varies from front to back to mimic anatomic femoral rollback during high degrees of flexion. For example, the major radius of the anterior surface 34 is preferably larger than the major radius of the posterior surface 38. Additionally, the major radius of the anterior and posterior surfaces may also reduce proceeding posteriorly. For example, in the embodiment shown in FIGS. 1-19, the anterior surfaces 34, 36 have gradually reducing major radii while the posterior surfaces 38, 40 have rapidly reducing major radii proceeding posteriorly. Proximate the posterior ends 29, 31 of the condyles 22, 24, the major radius is preferably greatly reduced to allow the prosthesis to flex preferably greater than 100 degrees, and more preferably more than 130 degrees. Further, the small radii of the ends 29, 31 prevent edge loading of the condyles 29, 31 while maintaining contact between the components on the tibial liner 60.

The condyles 22, 24 have a radius about the minor axis (minor axis) in the coronal plane. In a preferred embodiment, the condyles have a constant radius of curvature in the coronal plane. However, because the condylar surfaces are designed using NURBS, a more complex geometry can be provided wherein the radius of curvature in the coronal plane can vary. In particular, the posterior condylar surfaces can be designed with varying radii in all three planes.

Figure 8:
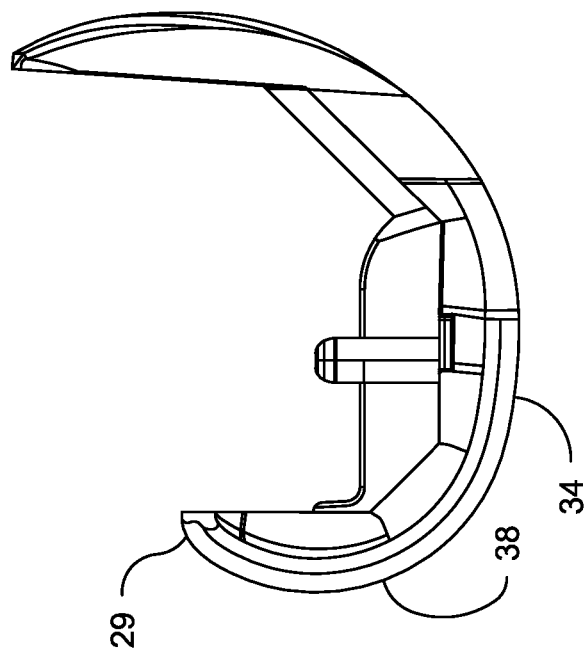
FIG. 8 is a medial elevation of the femoral component shown in FIG. 1.
Figure 7:
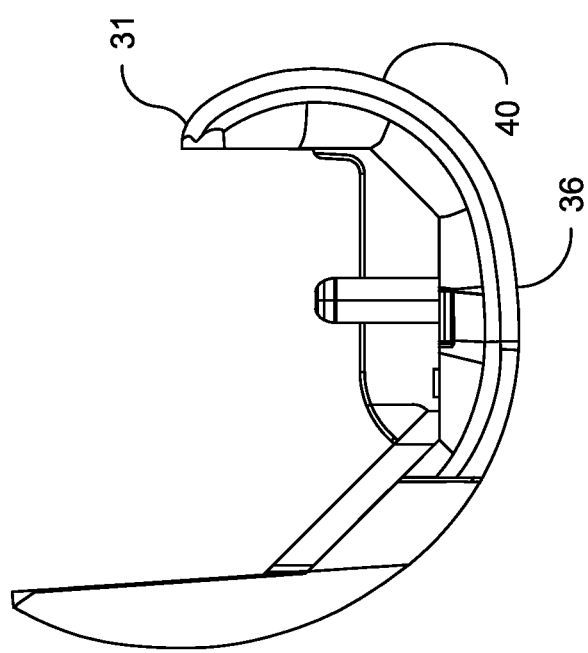
FIG. 7 is a lateral elevation of the femoral component shown in FIG. 1.

In one embodiment, the lateral condyle 24 has a larger major radius in the sagittal plane than the medial condyle 22 as seen in FIGS. 7-8. As described in greater detail below, the larger lateral condyle 24 helps the tibia to rotate axially as the femoral component translates posteriorly on the tibial component. However, it should be appreciated that the condyles 22, 24 could have the same major radius in the sagittal plane and still effect axial tibial rotation and femoral translation.

Figure 14:
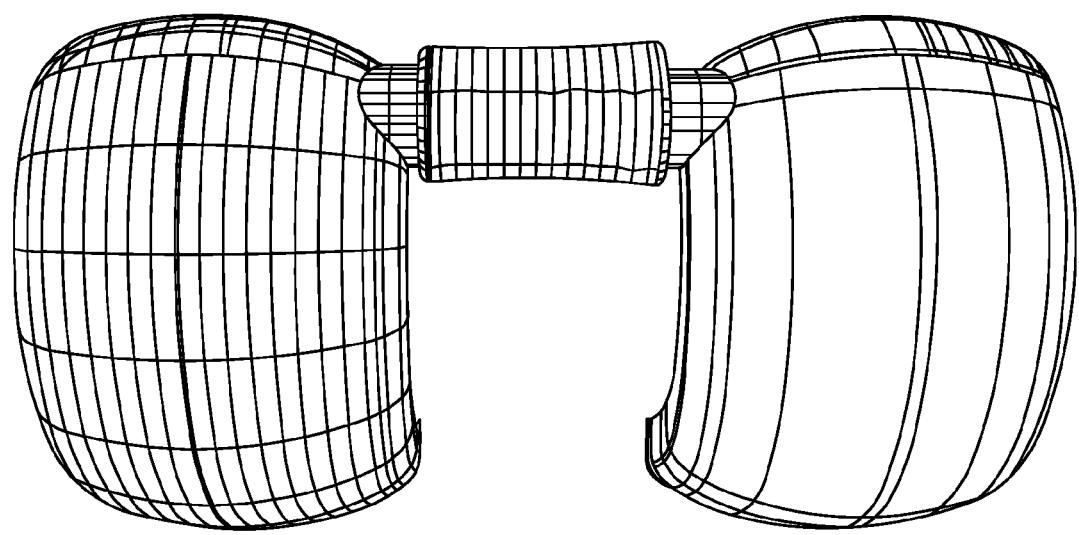
FIG. 14 is an enlarged posterior elevation of the femoral component illustrating with u and v isocurves the NURBS surfaces of the condylar portions and the cam.
Figure 16:
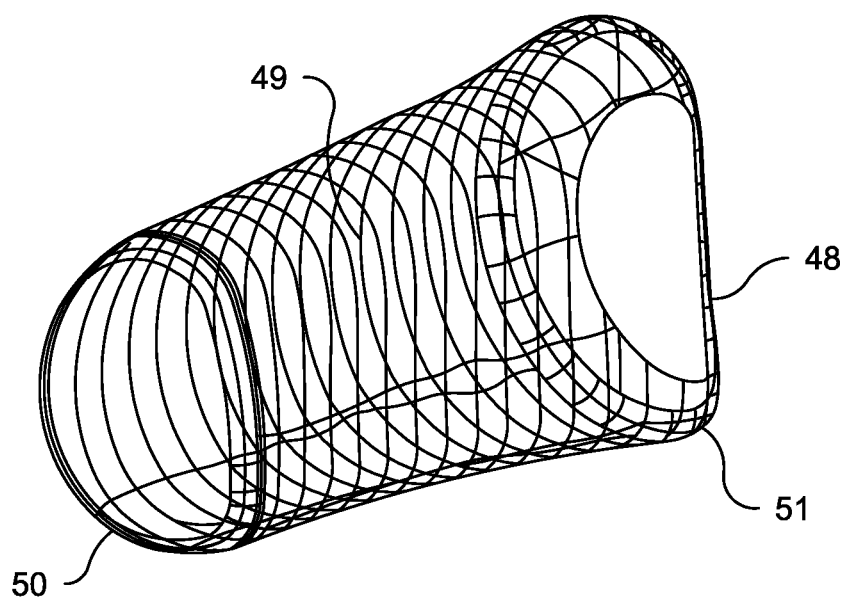
FIG. 16 is a perspective of the cam illustrating with u and v isocurves the NURBS surfaces of the curved front bearing surface and end surface.

As best seen in FIGS. 5 and 14, a cam 47 bridges and connects the posterior ends 29, 31 of the medial 22 and lateral 24 condyles. Referring to FIG. 16, the cam 47 has a generally flat back surface 48 and a curved front bearing surface 49. The back surface 48 is oriented coplanar with the back (proximal) surface of the condyles 22, 24 and is flat to abut the resected surface of the distal femur. As best seen in FIG. 5, the radius of curvature of the bearing surface 49 is larger at the lateral end 51 than the medial end 50. As described in greater detail below, the cam 47 engages the central post 90 on the tibial bearing liner 60 to provide stability and tibial rotation as the knee is flexed.

Figure 1:
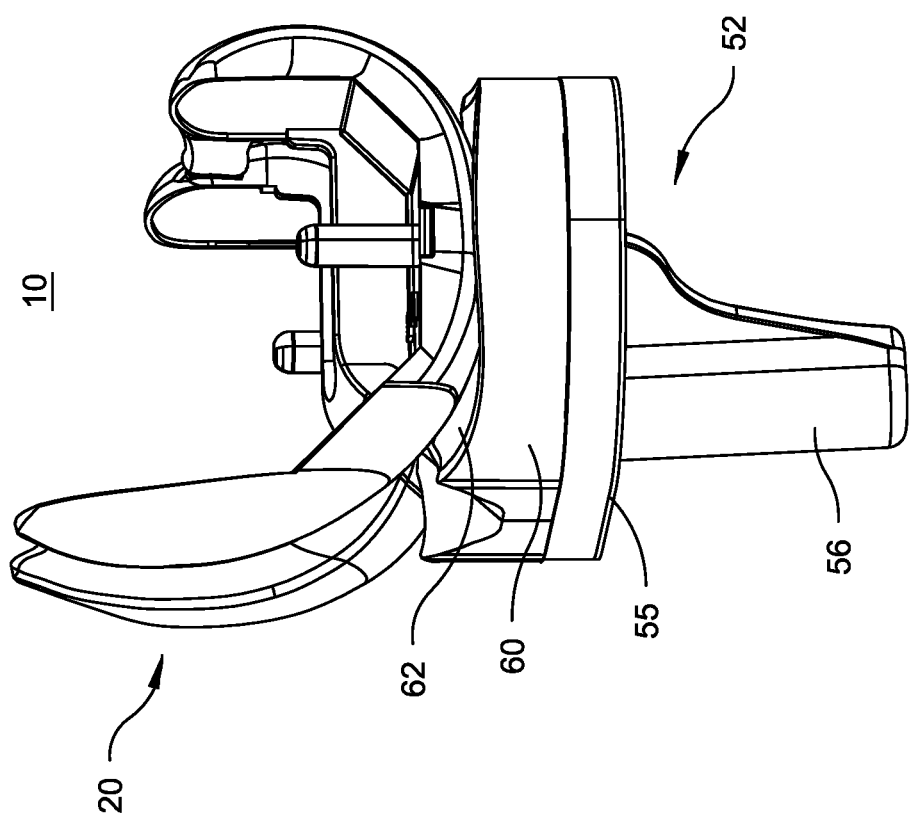
FIG. 1 is a perspective of a knee prosthesis in full flexion in accordance with an embodiment of the invention.
Figure 4:
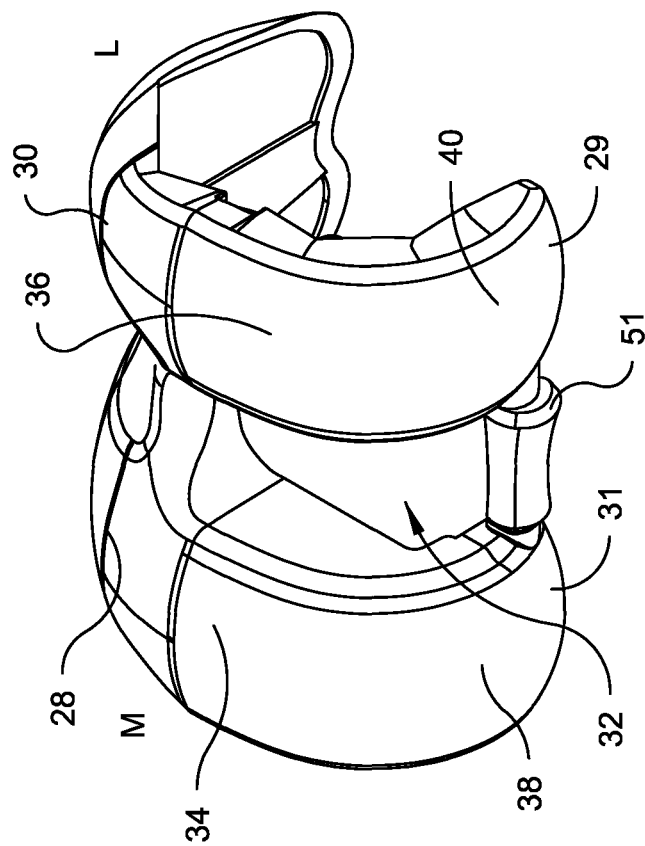
FIG. 4 is a perspective showing the anterior and posterior condylar portions of the femoral component shown in FIG. 1.
Figure 3:
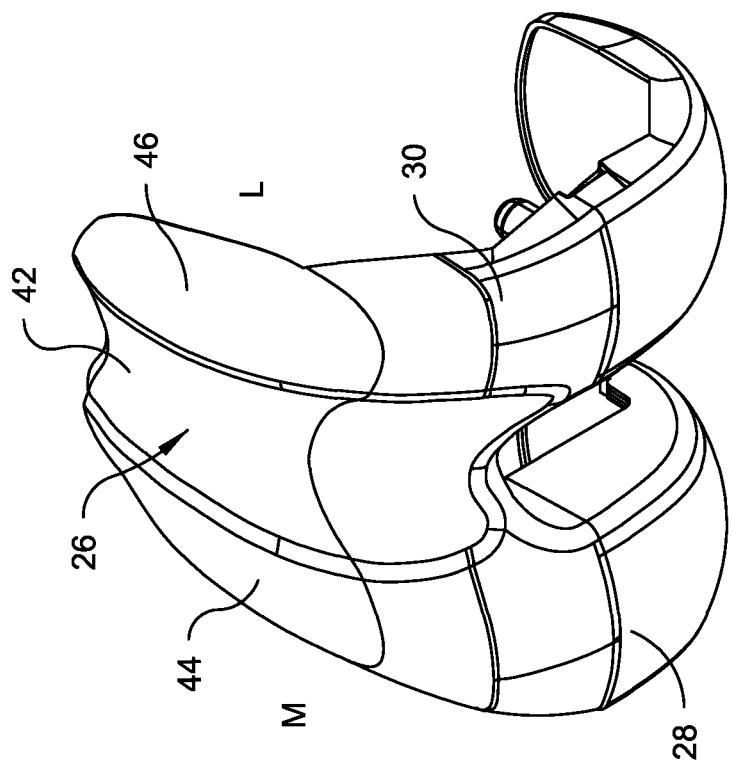
FIG. 3 is a perspective showing the patellar flange and anterior condylar portion of the femoral component shown in FIG. 1.

Referring to FIG. 1, the tibial component 52 generally comprises a tibial platform 54 and a liner 60. The tibial platform 54 has a base plate 55, which engages the distal surface 64 of the liner 60, and a stabilizing keel 56, which is inserted into the medullary canal of the tibia. The underside or distal surface of the base plate 55 has a textured, roughened surface that allows cement interdigitation during installation on the tibia.

The liner 60 has a proximal bearing surface 62, which articulates with the femoral component 20, and a distal surface 64, which abuts and is fixed to the tibial platform 52. The tibial component 50 also has a medial side 66, a lateral side 68, an anterior side 70, and a posterior side 72. The tibial component is generally symmetrical about a central sagittal axis running anterior to posterior.

Figure 17:
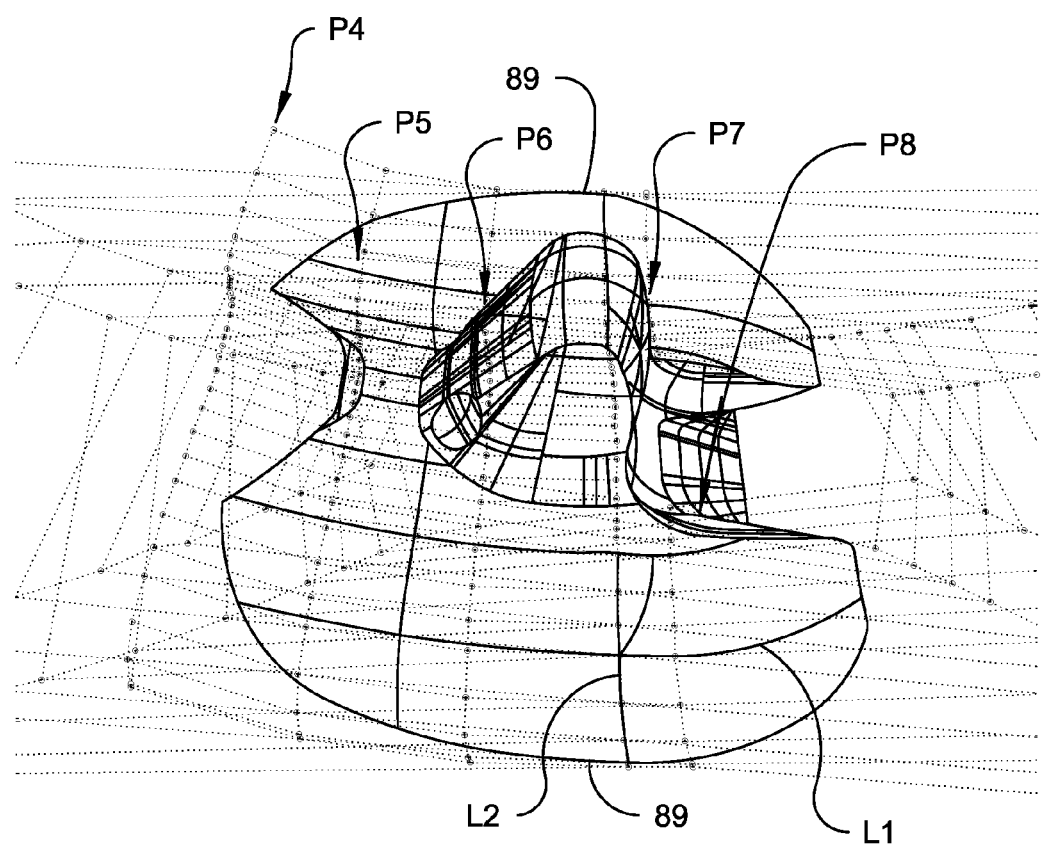
FIG. 17 is a perspective of the tibial liner illustrating with u and v isocurves the NURBS surfaces and illustrating the NURBS control points.
Figure 18:
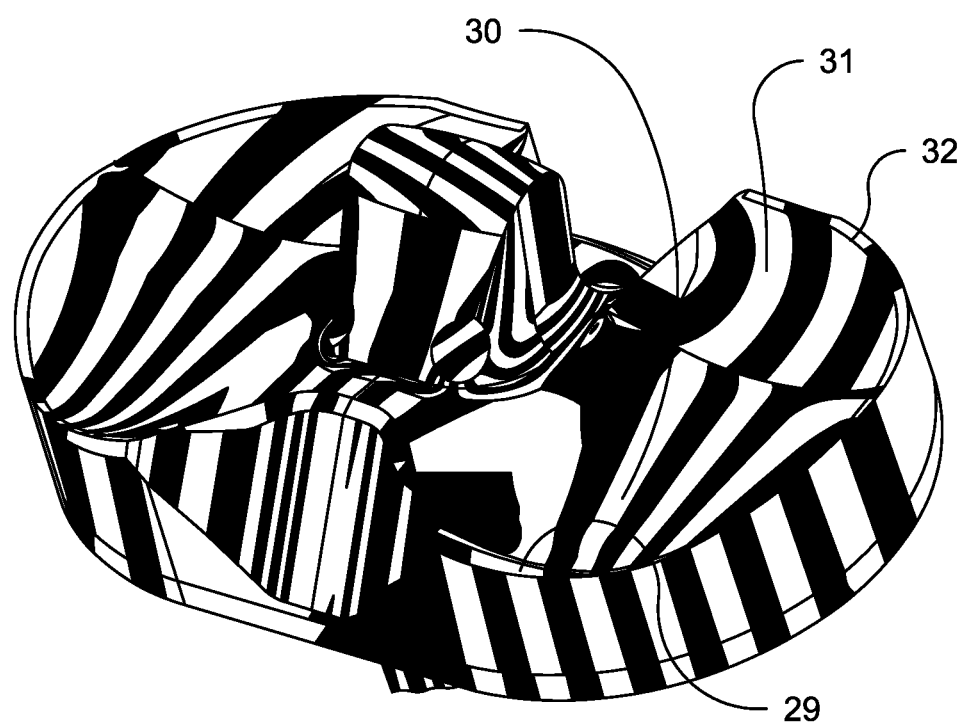
FIG. 18 is a perspective of the tibial liner showing a surface curvature zebra plot of the bearing surface.

A medial concavity 72 and a lateral concavity 74 are formed in the medial and proximal sides of the proximal surface 62. The medial 72 and lateral 74 concavities engage the medial 22 and lateral 24 condyles of the femoral component 20 as the components articulate relative to one another. In a preferred embodiment, the concavities 72, 74 are designed from different NURBS surfaces as best seen in FIGS. 17 and 18, although the entire proximal bearing surface 62 could also be constructed from a single NURBS surface as seen in FIGS. 21-24. In general, the concavities 72, 74 are more shallow than the depth of the femoral condyles 22, 24.

Each concavity 72, 74 generally comprises an anterior 76, 78 and posterior 80, 82 surface, respectively, that resemble toroidal sections, which blend together at an intermediate boundary. The anterior surfaces 76, 78 have a major radius of curvature oriented substantially in the sagittal plane. The posterior surfaces 80, 82 have a major radius of curvature oriented substantially in the transverse plane. The posterior concavities 80, 82 curve inwardly toward the sagittal central axis. Referring to FIG. 17, the midline isocurve L1 rotates around a central point that is slightly posterior to the post 90. As a result, the posterior surfaces 80, 82 sweep posteriorly and toward the central sagittal axis. The midline isocurve centerline L1 is continuous from the anterior concavity to the posterior concavity. The anterior 76, 78 and posterior 80, 82 surfaces have the same constant radius of curvature in the coronal plane and share the same tangent intersection "L2" in the coronal plane. The coronal curvature of the posterior surface is maintained as it turns toward the central sagittal axis. This construction allows the tibia to rotate about its longitudinal axis and translate posteriorly as the knee flexes.

The anterior and posterior concavities have a raised periphery at the anterior 86 and posterior 88 ends to contain and prevent dislocation of the femur from the tibia. The raised periphery also provides stability to the knee during flexion. As the condyles 22, 24 ride up the raised periphery of the concavities 72, 74, the collateral ligaments tighten and the knee becomes tighter.

The anterior concavities have lateral elevations 89, which contain the condyles 22, 24 so that the tibial component has little laxity during initial flexion and prevents tibial axial rotation. In contrast, the posterior concavities are designed without constraining lateral elevations and are designed to enable tibial axial rotation.

In the embodiment shown in FIGS. 1-19, the tibial component 60 includes central post 90, which has a proximal surface 91, anterior surface 92, posterior surface 93, medial side surface 94, and lateral side surface 95. The anterior surface 92 of the central post 90 is tapered at an angle relative to the distal surface 64 to minimize impingement of the patella or a patellar implant in deep flexion. The base 96 of the anterior surface 92 may be tapered at a different angle to minimize impingement of the intercondylar notch 32 in hyperextension.

Figure 19:
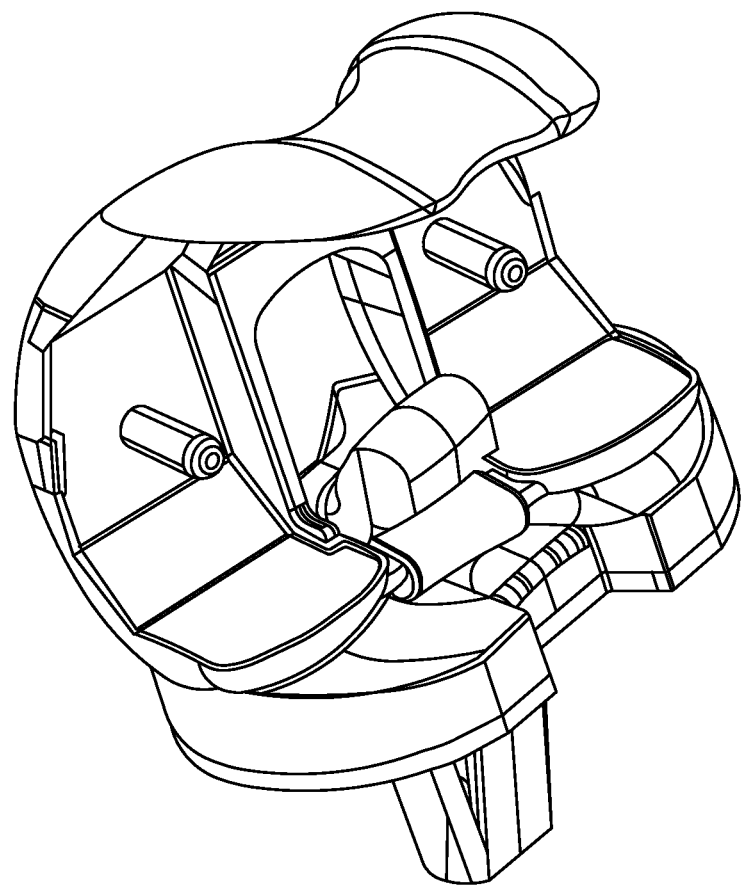
FIG. 19 is a perspective of the prosthesis in 90 degrees of flexion illustrating tibial axial rotation and femoral displacement.

Referring to FIGS. 1 and 19, the anterior surfaces 34, 36 of the condyles 22, 24 contact the tibial component in the range of full extension to an intermediate position in partial flexion. As the knee continues to flex, the posterior surfaces 38, 40 contact the tibial component from the intermediate position to full flexion.

Furthermore, when the knee flexes, the asymmetric cam 47 articulates with the tibial post 90 and causes the femoral component to translate posteriorly on the tibial component 52. In the embodiment illustrated in FIGS. 1-19, posterior translation of the femoral component is limited to about 1-2 millimeters. Referring to FIG. 19, the curved bearing surface 49 of the cam 47 also causes the tibia to rotate axially inwardly as the knee flexes. In a preferred embodiment, tibial rotation is enabled up to at least about 10 degrees, preferably up to at least about 15 degrees, more preferably up to about 20 degrees. However, the articulating surfaces could be designed to enable greater tibial axial rotation if desired. This complex translational and rotational movement is also enabled by the femoral condyles 22, 24 rotating in the posterior toroidal surfaces 80, 82. This embodiment of the prosthesis is used when both the anterior and posterior cruciate ligaments are surgically removed.

In addition to more accurately replicating the natural articular motion path of the human knee, the unique geometry of the articulating surfaces also reduces contact stress between the femoral condyles 22, 24 and the tibial liner 60 since the coronal curvature of the anterior section 76, 78 of the liner is the same as the coronal curvature of the posterior section 80, 82. Since the anterior and posterior curvature is the same, the condyles transition smoothly from front to back and do not exert excess stress on the liner 60.

As described above, the femoral component 20 and tibial liner 60 are modeled with NURBS surfaces created using Rhonocerous 3D design software. As can be seen from the various drawings, the use of NURBS enables very complex designs beyond standard geometries.

Figure 12:
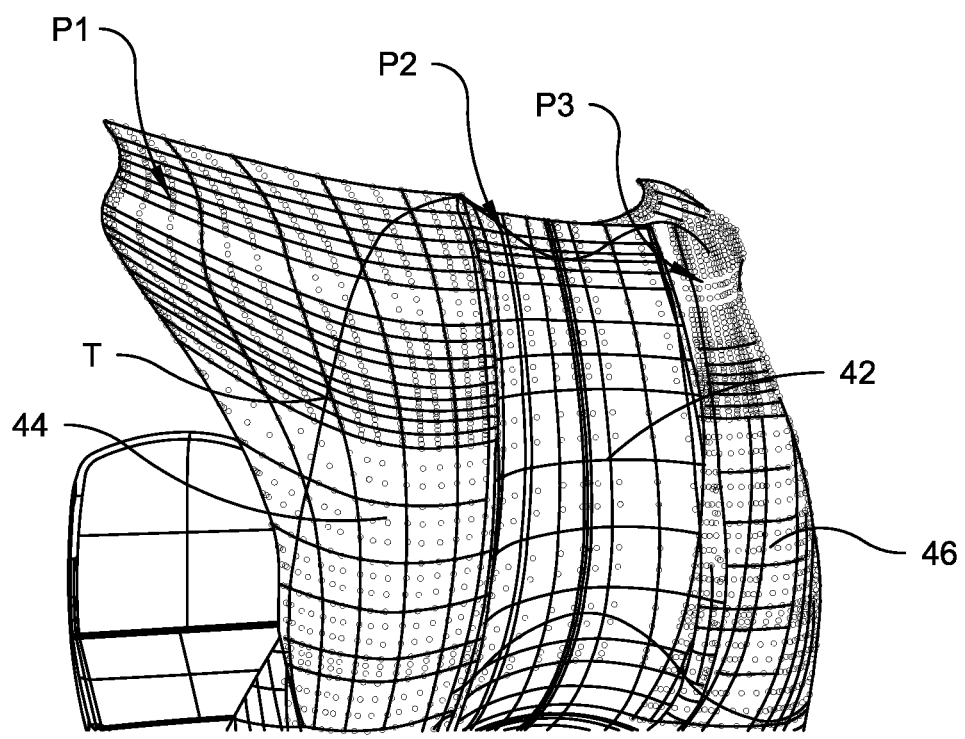
FIG. 12 is an enlarged perspective of the patellar flange portion of the femoral component illustrating the NURBS control points prior to trimming.

The discrete NURBS surfaces that define the patellar groove 42, and medial 44 and lateral 46 trochlear portions of the patellar flange 26 are illustrated with u and v isocurves in FIG. 11. The three-dimensional topography of the surface is illustrated after trimming. The complex $5^{th}$ order surface before trimming is shown in FIG. 12, which is trimmed by the $3^{rd}$ order patellar groove surface. FIG. 12 also illustrates the NURBS surface control points. By way of example, the surface of the patellar groove 42 is modeled using the following NURBS data: Points: −49.92, 9.06, 23.33; Normal Vector: −0.95, −0.24, −0.18; Radius of Curvature: 26.12 mm; and, Surface Area: 621.27 $mm^2$. The patellar groove is joined to the adjacent trochlear surfaces 44, 46, which are trimmed from a single surface modeled using the following NURBS data: Points: −51.36, 22.60, 15.84; Normal Vector: −0.91, 0.32, −0.26; Radius of Curvature: 6.60 mm; and, Surface Area: 546.13 $mm^2$. The patellar flange 26 also blends smoothly into the anterior condylar portions 22, 24. NURBS surface control points P1, P2, P3 are illustrated in FIG. 12 for the patellar flange portion 26 of the femoral component 20 prior to trimming. The medial 44 and lateral 46 trochlear surfaces are trimmed from a single NURBS surface along the trim line "T". By manipulating the control points, the three-dimensional topography of the surfaces can be changed in any direction.

Figure 13:
FIG. 13 is a perspective of the femoral component showing a surface curvature zebra plot of the patellar flange surface after shaping and trimming of the nubs surfaces.

The complex topography of the patellar flange is further illustrated by the surface curvature zebra plot shown in FIG. 13. The drawings show very complex curvatures and smooth transitions between the surfaces.

Figure 15:
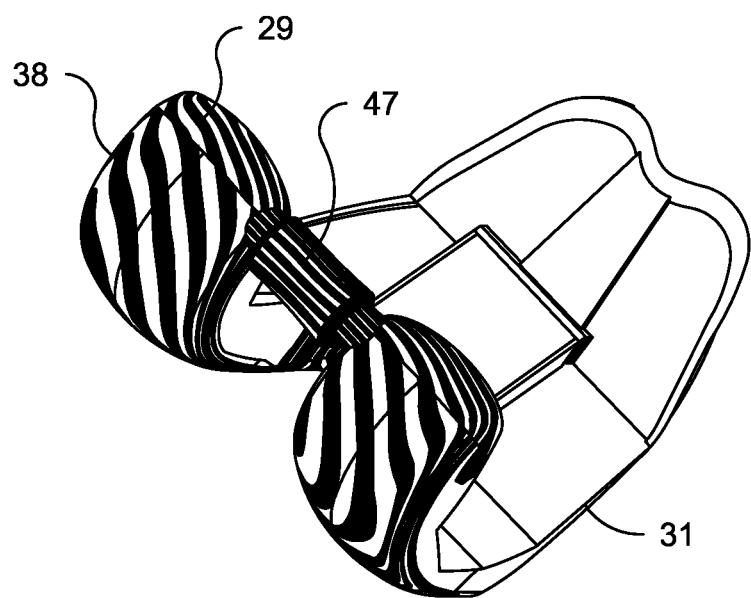
FIG. 15 is a perspective of the femoral component showing a surface curvature zebra plot of the posterior section of the condyles and the cam.

The discrete NURBS surfaces that define the posterior sections 38, 40 of the condyles 22, 24 are illustrated with u and v isocurves in FIG. 14 and a surface curvature zebra plot in FIG. 15. The distal and posterior condylar surfaces are substantially oriented in the sagittal direction and are curved in the coronal plane as well. By way of example, the distal and posterior condyles are defined by two surfaces using the following NURBS data: Points: 7.74; 16.08; 10.83; Normal Vector: 0.96; −0.24; −0.11; Radius of Curvature: 20.67 mm; and, Surface Area 535.27 $mm^2$. To enhance deep flexion, the radius of curvature in the sagittal plane decreases rapidly proceeding to the posterior end 29, 31 of the medial 22 and lateral 24 condyles. As best seen in FIG. 15, the posterior ends 29, 31 have very sharp radii compared to the anterior portion. The anterior sections 34, 36 blend into the posterior sections 38, 40 without abrupt transitions.

The discrete NURBS surfaces that define the cam 47 are illustrated by u and v isocurves in FIG. 16. The NURBS surfaces define the back surface 48, front bearing surface 49, medial end 50 and lateral end 51 surfaces.

The discrete NURBS surfaces that define the bearing surface of the liner 60 are shown with u and v isocurves in FIG. 17. NURBS surface control points P4, P5, P6, P7, P8 for the liner 60 are also illustrated in FIG. 17. The lateral edges 89 of the medial 72 and lateral 74 concavities are elevated by displacing the control points P4 at the periphery of the surface before trimming. The location and depth of the central depression can be changed by moving the control points P5 shown in FIG. 17. The elevation of the middle intercondylar region is controlled by moving the control points P6. The posterior surface curvature towards the center sagittal axis is obtained by moving the control points P7. The inner edges of the posterior surfaces are depressed inferiorly so that there is no restriction to femoral rotation by depressing the control points P8.

It should be readily apparent to those skilled in the art that the contour of any portion of the femoral condylar surfaces 22, 24, tibial bearing surface 62, curved cam bearing surface 49 can be easily manipulated by changing their respective control points to alter the articular motion path of the prosthesis. For example, the transverse curvature of the posterior sections of the concavities can be radiused around the tibial component center or may be offset by a distance that gives rise to a smaller or larger posterior articulating surface. A blend surface may be used between the anterior and posterior sections of the concavities. The height of the anterior 86 and posterior 88 ends of the concavities can also be varied to provide different amounts of anterior or posterior stability. The location of the deepest portion of the concavities 72, 74 can be placed anywhere on the tibial component 52 to alter the resting position of the femoral component under weight bearing load. The shape of the any of the individual surfaces can be altered as desired depending on the surgeon's preference and the patient's anatomy to control the motion path of the knee.

In contrast with common geometries arranged in the sagittal plane, or asymmetrical tibial articular surfaces with medial spherical and lateral ellipsoidal surfaces, the complex NURBS surfaces of the prosthesis 10 provide unlimited degrees of freedom in all three dimensions. Similarly, the patellar groove and trochlear surfaces can be shaped in three dimensions to allow natural tracking of the patella. For example, in another embodiment shown in FIG. 20, the patellar groove 142 and patellar trochlear surfaces 144, 146 are made from a single NURBS surface having a more shallow patellar groove.

The embodiment of the invention described above is designed for use when the anterior and posterior cruciate ligaments are surgically removed. In another embodiment shown in FIGS. 21-24, the prosthesis is designed for use when the posterior cruciate ligament is retained. In this embodiment, posterior displacement of the femur on the tibia is controlled by the posterior cruciate ligament and the NURBS surfaces are shaped such that there is no restriction to tibial axial rotation as the knee is flexed.

Figure 21:
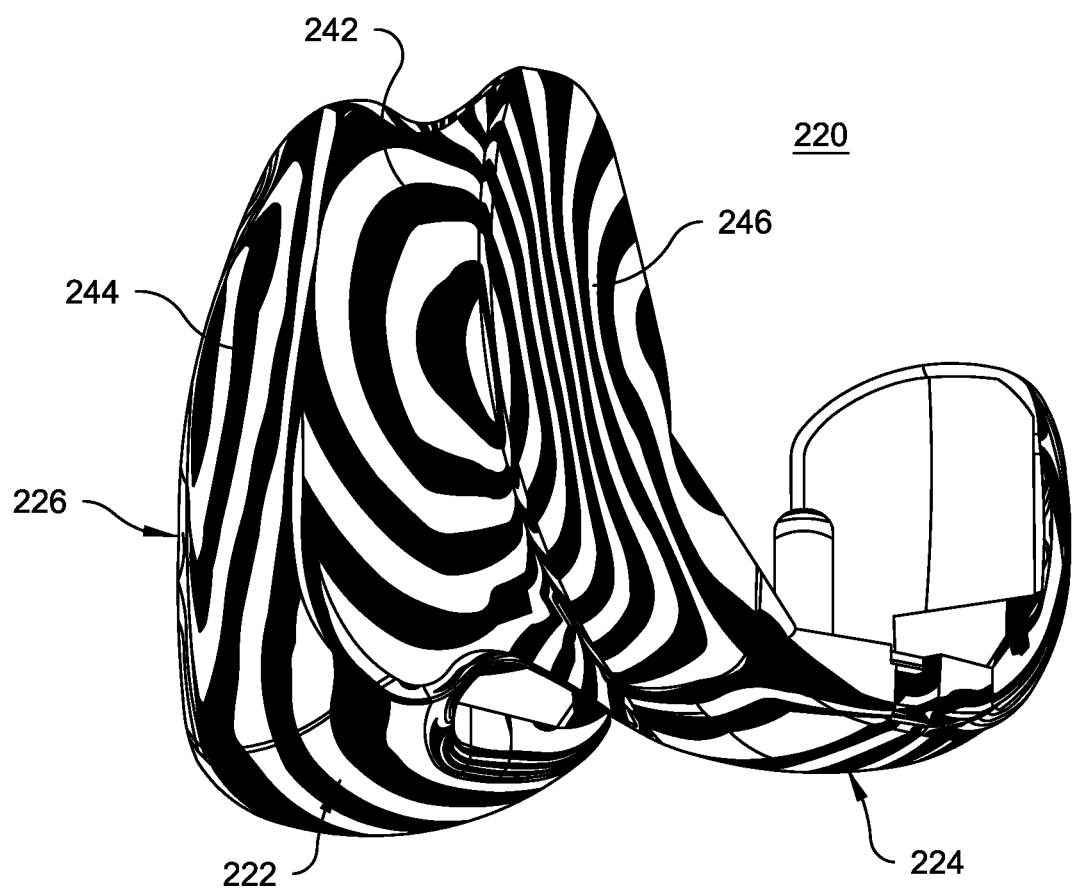
FIG. 21 is a perspective of the femoral component of a further embodiment of the invention showing a surface curvature zebra plot of the patellar flange.
Figure 22:
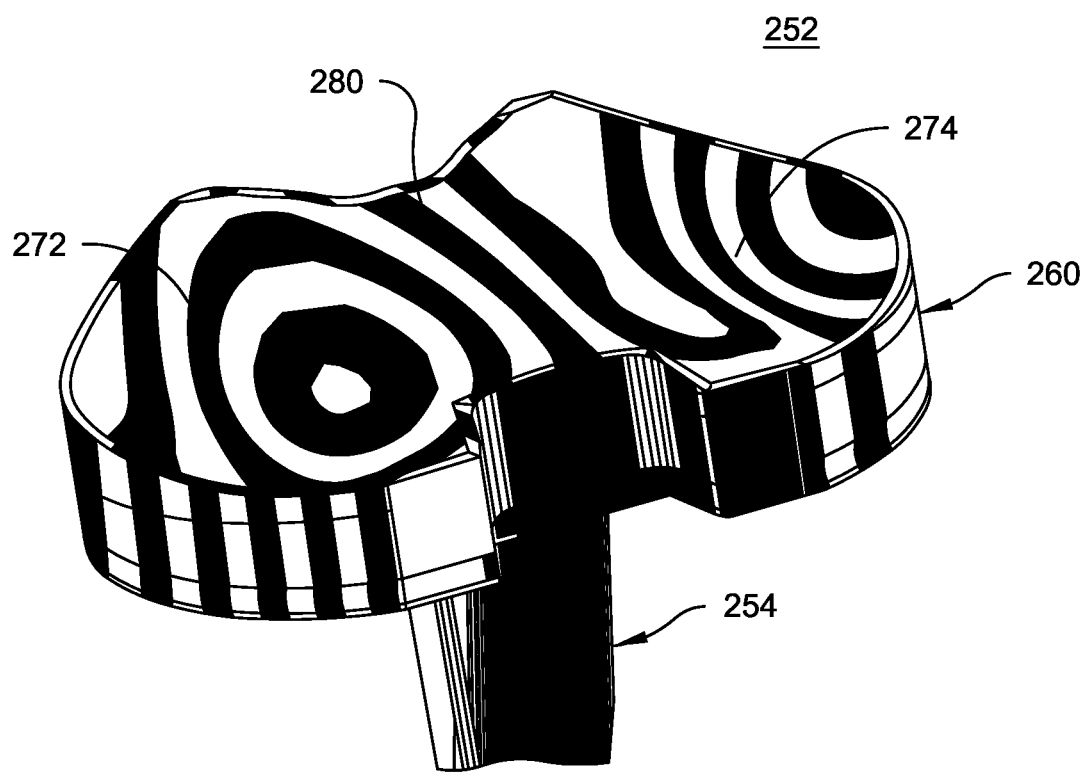
FIG. 22 is a perspective of the tibial component of a further embodiment of the invention showing a surface curvature zebra plot of the tibial liner.
Figure 23:
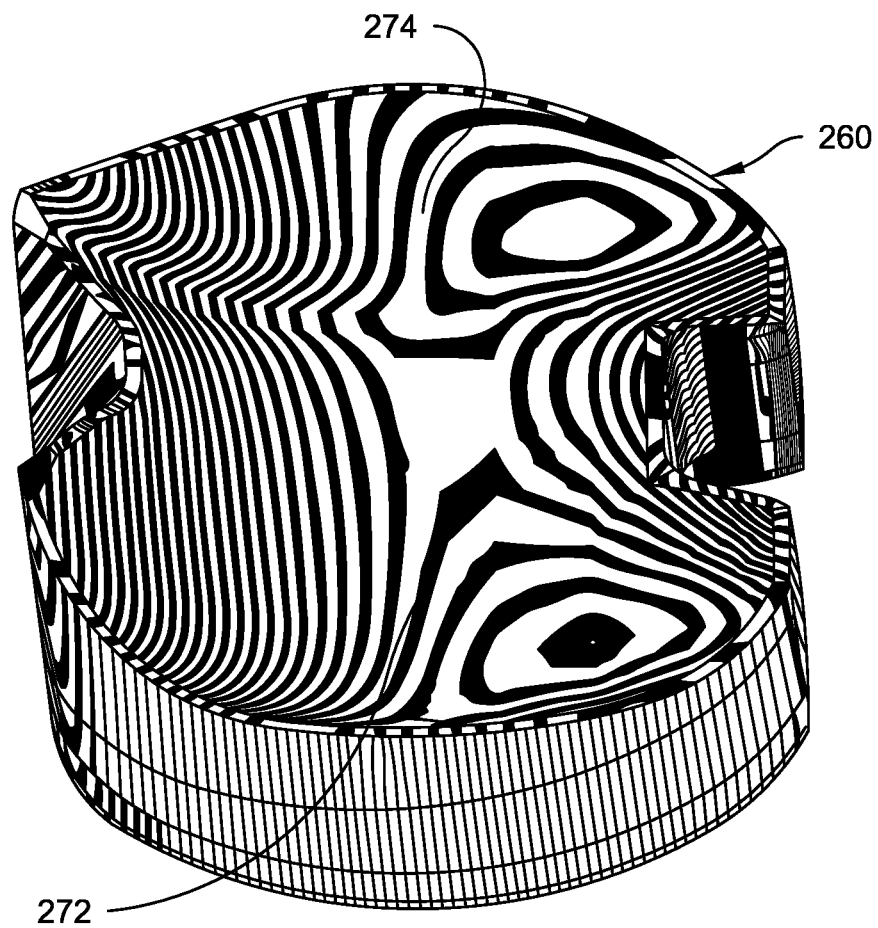
FIG. 23 is a perspective of the tibial liner shown of FIG. 22 showing a more detailed surface curvature zebra plot of the bearing surface of the liner; and, FIG. 24 is a perspective of the tibial liner of FIG. 22 illustrating with u and v isocurves the single NURBS surface of the bearing surface; and, FIG. 25 is a diagrammatic representation of a NURBS surface.
Figure 24:
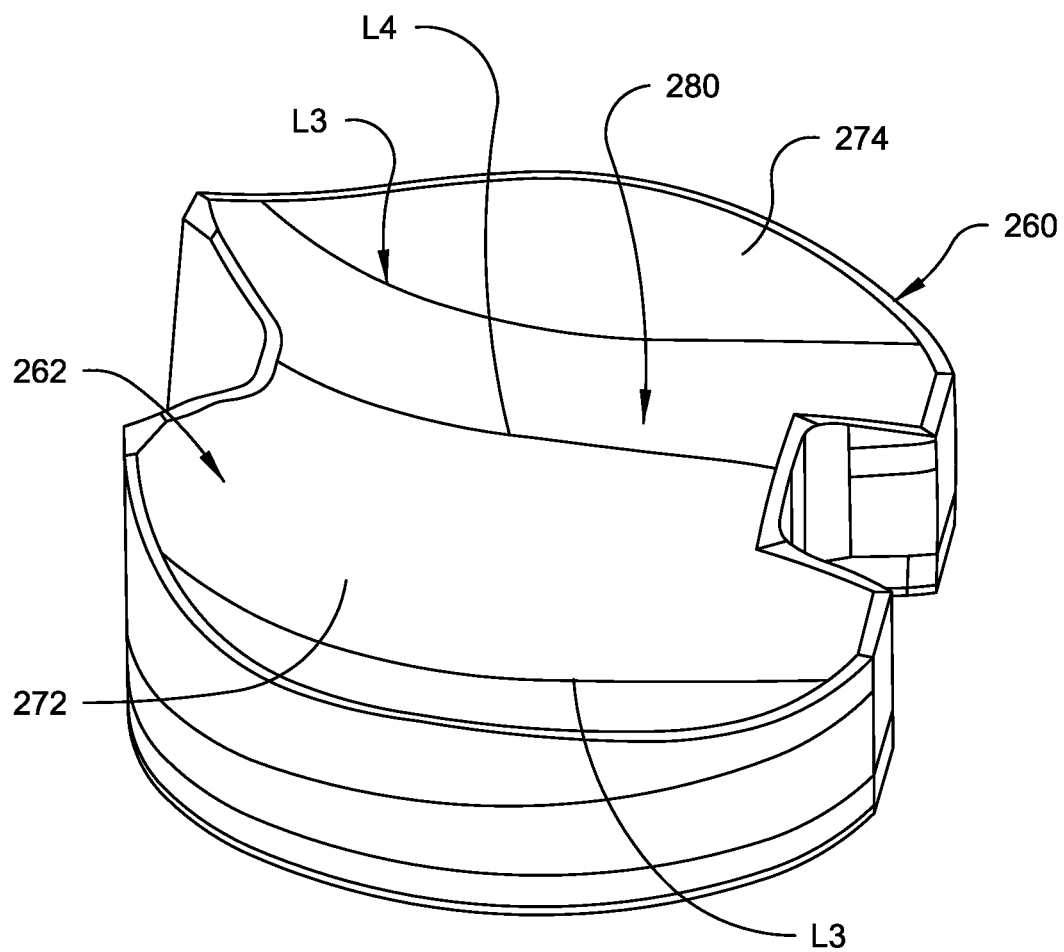
Figure 25:
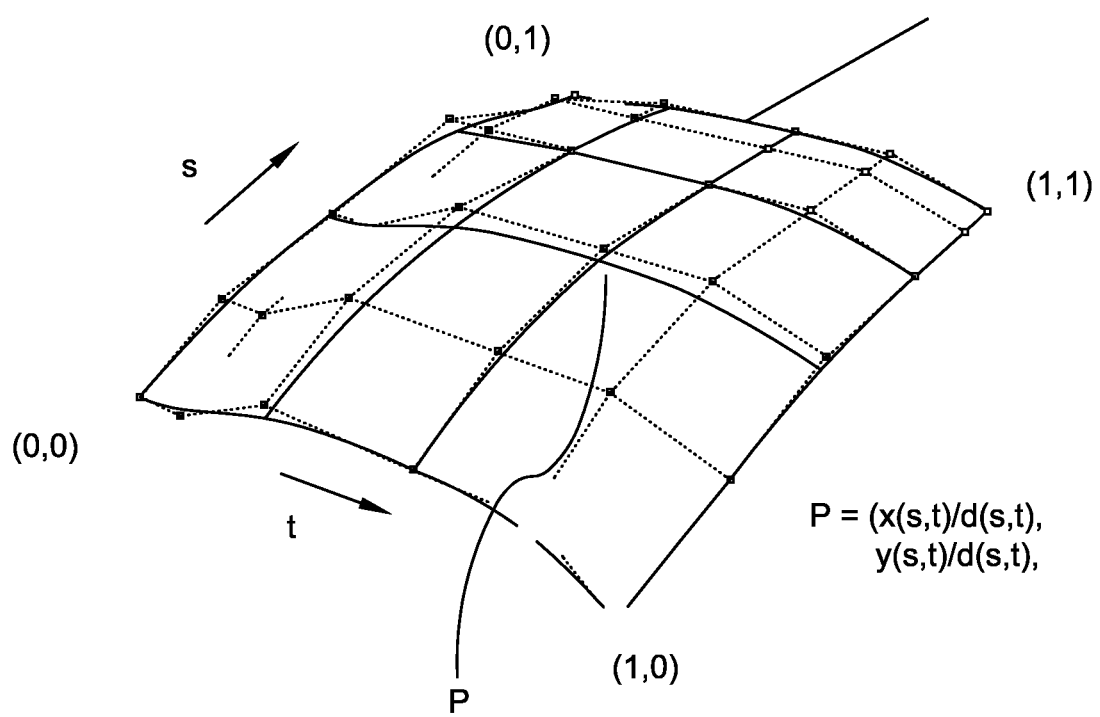

In the embodiment shown in FIGS. 21-24, the femoral component 220 has a similar construction to the femoral component 20 described with reference to FIGS. 1-19. The femoral component 220 includes medial 222 and lateral 224 condyles, and a patellar flange 226 with a patellar groove 242 and adjacent trochlear surfaces 244, 246. However, in this embodiment, the femoral component does not include a cam bridging the posterior ends of the condyles 222, 224. Compared to the first femoral component 20, the patellar groove 242 is deeper and the condyles 244, 246 more shallow in the coronal plane as seen in FIG. 21.

Likewise, the tibial component 252 has a similar construction to the tibial component 52 described with reference to FIGS. 1-19. The tibial component 252 includes a tibial platform 254 and a tibial bearing liner 260. The tibial liner has a proximal bearing surface 262 with medial 272 and lateral 274 concavities, which engage the medial 222 and lateral 224 condyles of the femoral component 220 as the components articulate relative to one another. However, in this embodiment, the center of the liner 260 does not include a central post, but is elevated gradually to provide medial-lateral stability.

Compared to the embodiment shown in FIGS. 1-19, the concavities 272, 274 are more elevated anteriorly to prevent forward sliding of the femur during flexion. The deepest portion of the concavities is shifted posteriorly and has elevations anteriorly and laterally to allow the femoral component to translate posteriorly and the tibial component to rotate axially as the prosthesis is flexed. In this embodiment, the bearing surface 262 of the liner 260 is designed from a single NURBS surface. The middle of the concavities 272, 274 in the sagittal plane is shown by the isocurve L3 curing posteriorly toward the center sagittal axis. A central tibial eminence 280, which prevents medial and lateral translation of the femur, is shown by the isocurve L4. In this embodiment, the intact posterior cruciate ligament controls posterior femoral displacement and internal tibial rotation. The articulating surfaces are designed with NURBS surfaces to avoid interference with the motion path dictated by the posterior cruciate ligament. The entire bearing surface 262 is less conforming to the condyles 222, 224 than in the first embodiment designed for posterior cruciate substitution.

The femoral component and tibial component may be constructed in various manners and from various materials. For example, the femoral component 20 and the tibial platform 54 may be machined, cast, forged or otherwise constructed as a one-piece integral unit from a medical grade, physiologically acceptable metal such as cobalt chromium alloy, stainless steel, titanium, titanium alloy or nickel cobalt alloy. Preferably, the femoral component and tibial platform are made using machinery that is compatible with NURBS modeling software.

The tibial liner may also be constructed in various manners and from various materials. For example, the tibial liner may be machined, molded or otherwise constructed as a one-piece, integral unit out of a medical grade, physiologically acceptable polymeric materials such as any polyolefin, including high-density polyethylene, low-density polyethylene, linear-low-density polyethylene, ultra-high molecular weight polyethylene (UHMWPE), or mixtures thereof. Polymeric materials, as used herein, also include polyethylene of various forms, for example, resin powder, flakes, particles, powder, or a mixture thereof, or a consolidated form derived from any of the above. Ultra-high molecular weight polyethylene (UHMWPE) refers to linear, non-branched chains of ethylene having initial average molecular weights in excess of about 500,000, preferably above about 1,000,000, and more preferably above about 2,000,000. Often the molecular weights can reach about 8,000,000 or more. The material can be treated, for example, by radiation, chemistry, or other technology to alter its wear properties and/or strength or hardness. Initial average molecular weight means the average molecular weight of the UHMWPE starting material, prior to any irradiation. It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A knee replacement prosthesis having anterior, posterior, lateral, medial, distal and proximal sides and sagittal, coronal and transverse planes, comprising:
   a) a femoral component that connects to the distal end of a resected femur, said femoral component including medial and lateral condyles having distal, articulating surfaces, and a patellar flange having a patellar articulating surface; and,
   b) a tibial component that connects to the proximal end of a resected tibia, said tibial component including a proximal bearing surface with medial and lateral concavities that articulate with said medial and lateral condyles;
   wherein said condylar articulating surfaces and said concavities are substantially defined by non-uniform, rational B-spline surfaces that enable anterior-posterior translation of the femur relative to the tibia and enable the tibia to rotate about its longitudinal axis during flexion of the knee.

2. The knee replacement prosthesis recited in claim 1, wherein axial tibial rotation is substantially restricted during initial flexion to an intermediate position, but is enabled after the prosthesis has been flexed beyond the intermediate position to full flexion.

3. The knee replacement prosthesis recited in claim 2, wherein the tibia rotates more than about 10 degrees axially after the prosthesis is fully flexed.

4. The knee replacement prosthesis recited in claim 1, wherein the condyles translate posteriorly in the concavities during flexion and anteriorly during extension.

5. The knee replacement prosthesis recited in claim 4, wherein the posterior translation is about 1-2 millimeters after the prosthesis is fully flexed.

6. The knee replacement prosthesis recited in claim 1, wherein said tibial concavities have multiple radii of curvature.

7. The knee replacement prosthesis recited in claim 6, wherein said tibial concavities have at least a first radius of curvature in the sagittal plane and at least a first radius of curvature in the coronal plane that is larger than the sagittal radius of curvature.

8. The knee replacement prosthesis recited in claim 7, wherein said concavities have multiple radii of curvature in the sagittal plane.

9. The knee replacement prosthesis recited in claim 1, wherein said condylar articulating surfaces have multiple radii of curvature.

10. The knee replacement prosthesis recited in claim 9, wherein the anterior portion of said condylar articulating surfaces has at least a first radius of curvature in the sagittal plane and the posterior portion has at least a first radius of curvature in sagittal plane that is smaller than the first anterior radius of curvature.

11. The knee replacement prosthesis recited in claim 10, wherein each of the anterior portion and the posterior portion of the condylar articulating surfaces has multiple radii of curvature in the sagittal plane.

12. The knee replacement prosthesis recited in claim 10, wherein the posterior portion of each condylar articulating surface is shaped to allow flexion greater than 100 degrees.

13. The knee replacement prosthesis recited in claim 1, wherein said tibial component (52) comprises a base having distal and proximal surfaces, and a liner having a distal surface that engages the proximal surface of the base and a proximal surface forming said bearing surface that engages and articulates with the femoral component (20).

14. The knee replacement prosthesis recited in claim 13, wherein said base comprises a base plate that rests on the tibial plateau, and a keel fixed to the distal surface of the base plate that can be inserted into the proximal tibial medullary canal.

15. The knee replacement prosthesis recited in claim 14, wherein the distal surface of said plate has a textured, roughened surface.

16. The knee replacement prosthesis recited in claim 1, wherein anterior and posterior translation of the femoral component (20) relative to the tibial component (52) is controlled by the posterior cruciate ligament.

17. The knee replacement prosthesis recited in claim 1, wherein tibial rotation is controlled by the posterior cruciate ligament.

18. The knee replacement prosthesis recited in claim 1, wherein said femoral component (20) includes a cam connecting the posterior ends of the condyles, and said tibial component (52) includes a central post intermediate said concavities.

19. The knee replacement prosthesis recited in claim 18, wherein anterior and posterior translation of the femoral component (20) relative to the tibial component (52) is controlled by said cam and central post.

20. The knee replacement prosthesis recited in claim 18, wherein rotation of the tibia about its longitudinal axis is controlled by said cam and central post.

21. The knee replacement prosthesis recited in claim 18, wherein contact between the cam and post occurs at knee flexion greater than about 30 degrees.

22. The knee replacement prosthesis recited in claim 1, wherein said patellar surface is substantially defined by non-uniform, rational B-spline.

23. The knee replacement prosthesis recited in claim 22, wherein the patellar surface includes a laterally-angled patellar groove and raised trochlear surfaces on each side of the groove.

24. A knee replacement prosthesis having anterior, posterior, lateral, medial, distal and proximal sides and sagittal, coronal and transverse planes, comprising:
a) a femoral component that connects to the distal end of a resected femur, said femoral component including medial and lateral condyles having distal, articulating surfaces, and a patellar flange having an articulating patellar surface; and,
b) a tibial component that connects to the proximal end of a resected tibia, said tibial component including a proximal bearing surface with medial and lateral concavities that articulate with said medial and lateral condyles;
wherein said prosthesis enables anterior-posterior translation of the femur relative to the tibia, and
wherein said prosthesis restricts axial tibial rotation during initial flexion to an intermediate point and enables axial tibial rotation after the prosthesis has been flexed beyond the intermediate position to full flexion.

25. The knee replacement prosthesis recited in claim 24, wherein said condylar articulating surfaces and said concavities are substantially defined by non-uniform, rational B-spline surfaces.

26. A knee replacement prosthesis having anterior, posterior, lateral, medial, distal and proximal sides and sagittal, coronal and transverse planes, comprising:
a) a femoral component that connects to the distal end of a resected femur, said femoral component including medial and lateral condyles having distal, articulating condylar surfaces, and a patellar flange having an articulating patellar surface; and,
b) a tibial component that connects to the proximal end of a resected tibia, said tibial component including a proximal bearing surface with medial and lateral concavities that articulate with said medial and lateral condyles;
wherein said condylar surfaces and said concavities are substantially defined by high order nonrational B spline surfaces.

27. The prosthesis recited in claim 26, wherein said patellar flange is substantially defined by high order nonrational B spline surfaces.

28. The prosthesis recited in claim 27, wherein said prosthesis enables full flexion of greater than 100 degrees, and enables tibial axial rotation of more than 10 degrees and femoral posterior translation of about 1-2 mm. after full flexion.

29. A method of making a knee replacement prosthesis having anterior, posterior, lateral, medial, distal and proximal sides and sagittal, coronal and transverse planes, comprising the steps of:
a) a femoral component that connects to the distal end of a resected femur, said femoral component including medial and lateral condyles having distal, articulating surfaces, and a patellar flange having a patellar articulating surface; and,
b) a tibial component that connects to the proximal end of a resected tibia, said tibial component including a proximal bearing surface with medial and lateral concavities that articulate with said medial and lateral condyles;
c) modeling said condylar surfaces and said concavities using NURBS.

* * * * *